(12) United States Patent
Kira et al.

(10) Patent No.: US 10,509,033 B2
(45) Date of Patent: Dec. 17, 2019

(54) METHOD, KIT AND BIOMARKER FOR DIAGNOSING CHRONIC INFLAMMATORY DEMYELINATING POLYNEUROPATHY

(71) Applicant: Kyushu University, National University Corporation, Fukuoka (JP)

(72) Inventors: Junichi Kira, Fukuoka (JP); Nobutoshi Kawamura, Fukuoka (JP); Ryo Yamasaki, Fukuoka (JP); Dai Matsuse, Fukuoka (JP); Hidenori Ogata, Fukuoka (JP)

(73) Assignee: Kyushu University, National University Corporation, Fukuoka-shi, Fukuoka (JP)

( * ) Notice: Subject to any disclaimer, the term of this patent is extended or adjusted under 35 U.S.C. 154(b) by 0 days.

(21) Appl. No.: 15/544,756

(22) PCT Filed: Jan. 20, 2016

(86) PCT No.: PCT/JP2016/051606
§ 371 (c)(1),
(2) Date: Nov. 27, 2017

(87) PCT Pub. No.: WO2016/117618
PCT Pub. Date: Jul. 28, 2016

(65) Prior Publication Data
US 2018/0074051 A1    Mar. 15, 2018

Related U.S. Application Data

(60) Provisional application No. 62/105,313, filed on Jan. 20, 2015.

(51) Int. Cl.
*G01N 33/566* (2006.01)
*C07K 16/28* (2006.01)
*G01N 33/564* (2006.01)
*G01N 33/58* (2006.01)

(52) U.S. Cl.
CPC ....... *G01N 33/564* (2013.01); *C07K 16/2803* (2013.01); *G01N 33/582* (2013.01); *G01N 2333/705* (2013.01); *G01N 2800/285* (2013.01)

(58) Field of Classification Search
None
See application file for complete search history.

(56) References Cited

U.S. PATENT DOCUMENTS

| | | | | |
|---|---|---|---|---|
| 8,735,553 B1 * | 5/2014 | Li | | C07K 16/2803 |
| | | | | 424/144.1 |
| 2003/0158228 A1 * | 8/2003 | January | | A61K 31/445 |
| | | | | 514/317 |
| 2004/0142417 A1 * | 7/2004 | Wozney | | C07K 14/51 |
| | | | | 435/69.1 |
| 2005/0221280 A1 * | 10/2005 | Westwick | | C40B 30/04 |
| | | | | 435/4 |
| 2005/0249736 A1 * | 11/2005 | Krasnoperov | | C07K 14/715 |
| | | | | 424/155.1 |
| 2006/0141535 A1 * | 6/2006 | Weigel | | C07K 14/705 |
| | | | | 435/7.1 |
| 2006/0217535 A1 * | 9/2006 | Yuhas | | C07K 14/43563 |
| | | | | 530/350 |
| 2013/0172319 A1 * | 7/2013 | Grainger | | C07D 487/08 |
| | | | | 514/212.03 |

OTHER PUBLICATIONS

Ogata et al., Characterization of IgG4 anti-neurofascin 155 antibodypositive polyneuropathy, (2015) Annals of Clinical and Translational Neurology 2(10): 960-971.*
Condreay et al., Transient and stable gene expression in mammalian cells transduced with a recombinant baculovirus vector, Jan. 1999, Proc. Natl. Acad. Sci. USA vol. 96, pp. 127-132 (Year: 1999).*
Parham et al., Effects of pCIneo and pCEP4 expression vectors on transient and stable protein production in human and simian cell lines, 2001, Cytotechnology 35: 181-187 (Year: 2001).*
Ng, et al., "Neurofascin as a target for autoantibodies in peripheral neuropathies" 2012, Neurology, vol. 79, Issue No. 23, pp. 2241-2248.
Yamasaki, R., "Anti-neurofascin antibody in combined central and peripheral demyelination", 2013, Clinical & Experimental Neuroimmunology, vol. 4, Suppl. 1, pp. 68-75.
Querol, et al., "Neurofascin IgG4 antibodies in CIDP associate with disabling tremor and poor response to IVIg" 2014, Neurology, vol. 82, Issue No. 10, pp. 879-886.
Kawamura, et al.,"Anti-neurofascin antibody in patients with combined central and peripheral demyelination", 2013, Neurology vol. 81, Issue No. 8, pp. 714-722.
Notturno, et al., "Autoantibodies to neurofascin-186 and gliomedin in multifocal motor neuropathy" 2014, Journal of Neuroimmunology, vol. 276, Issue No. 1-2, pp. 207-212.
Search Report dated Apr. 19, 2016, issued by the International Searching Authority in counterpart International Patent Application No. PCT/JP2016/051606 (PCT/ISA/210).
Written Opinion dated Apr. 19, 2016, issued by the International Searching Authority in counterpart International Patent Application No. PCT/JP2016/051606 (PCT/ISA/237).

* cited by examiner

*Primary Examiner* — John D Ulm
(74) *Attorney, Agent, or Firm* — Sughrue Mion, PLLC

(57) ABSTRACT

Provided are a method for diagnosing chronic inflammatory demyelinating polyneuropathy (CIDP), in particular, a diagnostic method for specifically diagnosing a group having a specific pathophysiology among CIDPs, and a kit and a biomarker for use in such a diagnosis. The diagnostic method for diagnosing CIDP of the present invention includes a step of measuring an anti-neurofascin 155 antibody contained in a sample.

11 Claims, 7 Drawing Sheets
Specification includes a Sequence Listing.

ived in 2010.
METHOD, KIT AND BIOMARKER FOR DIAGNOSING CHRONIC INFLAMMATORY DEMYELINATING POLYNEUROPATHY

TECHNICAL FIELD

The present invention relates to a diagnostic method for specifically diagnosing chronic inflammatory demyelinating polyneuropathy, and a kit and a biomarker for use in such a diagnosis.

BACKGROUND ART

Chronic inflammatory demyelinating polyneuropathy (hereinafter, also referred to as CIDP) is a peripheral nerve disease which features chronic progressive, chronic stepped or recurrent bilateral muscle weakness and sensation disturbance over 2 months or more in distal or proximal muscles of extremities as cardinal symptoms. The pathogenesis of CIDP is thought to be an autoimmune disease caused by immune abnormality to the constituent components of peripheral nerve myelin, details of which are not yet known.

At present, the guidelines proposed by the European Federation of Neurological Societies Peripheral Nerve Society (EFNSPNS) revised in 2010 are often used for the diagnosis of CIDP which has been carried out based on comprehensive judgment of clinical symptoms, electrophysiological criteria, cerebrospinal fluid findings, nerve root hypertrophy on MRI, and the like.

On the other hand, CIDP disease-specific biomarkers have not been reported to date. In addition, autoantibody-positive neuropathy for myelin-associated glycoprotein (MAG) is regarded as an independent disease, and it is excluded from CIDP.

CIDP is assumed to be a syndrome involving various pathological conditions since the progress, response to therapy and prognosis vary from case to case, and there is an urgent need in the art to establish a therapeutic regimen according to each pathological condition of CIDP.

The present inventors have found that the serum from the case of combined central and peripheral demyelination (CCPD), which is a rare disease causing demyelination in both the central nervous system and the peripheral nervous system, is positive for an anti-neurofascin 155 (NF155) antibody (Non-Patent Document 1). It has also been reported that the anti-NF155 antibody is positive in a small portion (about 4%) of CIDP (Non-Patent Documents 2 and 3).

However, the above reports are merely a small number of studies and no comparison between antibody-positive CIDP and antibody-negative CIDP has been made. For these reasons, it was unknown whether or not a specific subtype in CIDP becomes positive, and whether or not such a specific subtype in CIDP is associated with the clinical feature.

RELATED ART

Non-Patent Documents

[Non-Patent Document 1] Neurology. 2013 Aug. 20; 81(8): pp 714 to 22
[Non-Patent Document 2] Neurology. 2012 Dec. 4; 79(23): pp 2241 to 8
[Non-Patent Document 3] Neurology. 2014 Mar. 11; 82(10): pp 879 to 86

DISCLOSURE OF INVENTION

Problems to be Solved by the Invention

As described above, conventional diagnosis of CIDP has been often carried out using the guidelines proposed by the European Federation of Neurological Societies Peripheral Nerve Society (EFNSPNS) revised in 2010.

Further, diagnosis of CIDP has been carried out based on comprehensive judgment of clinical symptoms, electrophysiological criteria, cerebrospinal fluid findings, nerve root hypertrophy on MRI, and the like, and biomarkers highly specific to CIDP have not yet been reported. In addition, CIDP is assumed to be a syndrome involving various pathological conditions, and there is an urgent need to establish a biomarker and a therapeutic regimen corresponding to each pathological condition of CIDP.

With regard to Guillain-Barré syndrome (hereinafter, also referred to as GBS), which acutely affects peripheral nerves, it is difficult to distinguish GBS at the first episode from CIDP. The therapeutic regimen is also different therebetween. For these reasons, there is a need for a biomarker distinguishing between GBS and CIDP, but no such a biomarker has been reported so far.

Furthermore, in the case where CCPD develops in central nervous lesions, it has been difficult to distinguish CCPD from multiple sclerosis (hereinafter, also referred to as MS), which is a demyelinating disease that affects only central nerves. In the treatment of MS, an interferon beta (IFNβ) preparation is effective, but in CCPD, the IFNβ preparation is ineffective and exacerbates the symptoms in about 30% of cases as well. Accordingly, there is a need for a biomarker distinguishing therebetween.

As can be seen from the foregoing, it is extremely important to develop a method for diagnosing CIDP, but a method for accurately diagnosing CIDP has not been established so far. Also, no biomarker for use in such a method has been reported in the past, and determining the presence or absence of such an antibody that specifically binds to NF155 is important in diagnosing CIDP. Accordingly, an object of the present invention is to provide a diagnostic method for diagnosing CIDP, in particular, a diagnostic method for specifically diagnosing a group having a specific pathophysiology among CIDPs, and a kit and a biomarker for use in such a diagnosis.

Means for Solving the Problems

The present inventors have found that an antibody reacting with NF155 is present in a sample of some CIDP patients and have found that CIDP can be diagnosed by measuring the antibody reacting with NF155. That is, the present inventors have found that, by measuring an antibody reacting with NF155, it is possible to establish a therapeutic regimen corresponding to each pathological condition for CIDP involving various pathological conditions. The present invention has been completed based on these findings.

That is, the present invention relates to the following (1) to (15).

(1) A method for diagnosing chronic inflammatory demyelinating polyneuropathy, comprising measuring an anti-neurofascin 155 antibody contained in a sample.

(2) The diagnostic method described in (1), further comprising measuring an anti-neurofascin 186 antibody contained in the sample.

(3) The diagnostic method described in (2), comprising detecting an antibody which reacts with neurofascin 155, but does not react with neurofascin 186.
(4) The diagnostic method described in any one of (1) to (3), comprising bringing the sample into contact with cells with forced expression of neurofascin 155 and cells with forced expression of neurofascin 186 and measuring the presence of the anti-neurofascin 155 antibody and/or the anti-neurofascin 186 antibody using a fluorescently labeled anti-human IgG antibody.
(5) The diagnostic method described in (4), which is carried out by a flow cytometry technique.
(6) The diagnostic method described in any one of (1) to (5), comprising distinguishing chronic inflammatory demyelinating polyneuropathy from Guillain-Barré syndrome or multiple sclerosis.
(7) The diagnostic method described in any one of (1) to (6), wherein the sample is blood or cerebrospinal fluid.
(8) A method for measuring an anti-neurofascin 155 antibody and/or an anti-neurofascin 186 antibody in a sample, comprising bringing a sample into contact with cells with forced expression of neurofascin 155 and cells with forced expression of neurofascin 186 and measuring the presence of the anti-neurofascin 155 antibody and the anti-neurofascin 186 antibody using a fluorescently labeled anti-human IgG antibody.
(9) The method described in (8), which is carried out by a flow cytometry technique.
(10) The method described in (8) or (9), comprising selecting a sample in which an anti-neurofascin 155 antibody is present but an anti-neurofascin 186 antibody is absent.
(11) The method described in any one of (8) to (10), wherein the sample is blood or cerebrospinal fluid.
(12) A kit for diagnosing chronic inflammatory demyelinating polyneuropathy, comprising a cell line with forced expression of neurofascin 155.
(13) The kit described in (12), further comprising a cell line with forced expression of neurofascin 186.
(14) The kit described in (12) or (13), further comprising a fluorescently labeled anti-human IgG antibody.
(15) A biomarker for diagnosing chronic inflammatory demyelinating polyneuropathy, comprising an anti-neurofascin 155 antibody.

Effects of the Invention

According to the present invention, it has become possible to achieve diagnosis of CIDP by detecting an anti-NF155 antibody in a sample. In particular, according to the present invention, it has become possible to extract a group of patients having the same pathophysiology by measuring an anti-NF155 antibody and an anti-NF186 antibody in a sample of an inflammatory demyelinating disease case and extracting a positive case that reacts only with NF155. Although CIDP, which is a disease group having various pathological conditions, showed various therapeutic effects in each case, it has become possible to provide a more appropriate therapeutic regimen by selecting a case having an anti-NF155 antibody.

Further, according to the present invention, it is also possible to distinguish GBS from CIDP and to distinguish MS from CCPD.

Then, by measuring an anti-NF155 specific antibody in a sample (for example, serum or cerebrospinal fluid), the measurement results of such an antibody become an index of diagnosis and therapeutic effect judgment. If the significance of an anti-NF155 antibody is recognized worldwide, like anti-MAG antibody-positive neuropathy, anti-NF155 antibody-positive neuropathy may be established as a disease concept independent from CIDP.

BRIEF DESCRIPTION OF DRAWINGS

In FIG. 1B, the serum dilution ratios are 1:20, 1:100, 1:200, 1:400, 1:800, 1:1600, 1:3200, 1:6400, and 1:12800.

In FIGS. 5A and 5B, the leftmost view represents a normal control.

FIGS. 6A and 6B show demyelinating lesions at the cerebral horizontal section, and FIG. 6C is a view of the cerebral sagittal section which shows the lesion in FIG. 6A.

EMBODIMENTS FOR CARRYING OUT THE INVENTION

[Chronic Inflammatory Demyelinating Polyneuropathy (CIDP)]

Figure 1:
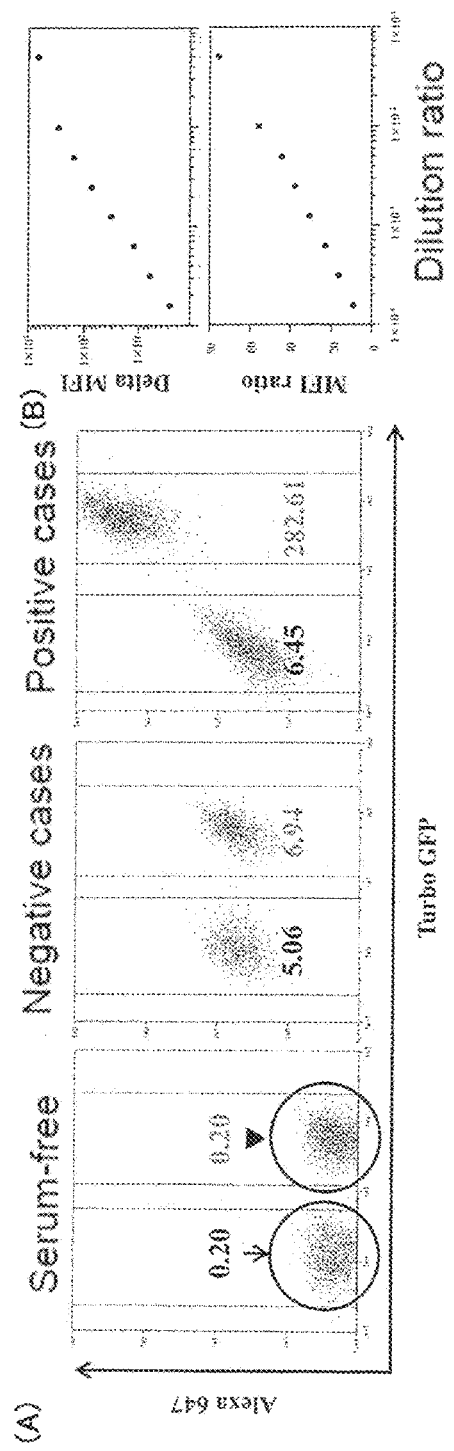
FIG. 1A is a view showing the results of anti-NF155 antibody measurement by a flow cytometry technique.
FIG. 1B is a view showing the relationship between dilution ratio of serum of an anti-NF155 antibody-positive CIDP patient and delta MFI value (upper) and the relationship between dilution ratio of serum of an anti-NF155 antibody-positive CIDP patient and MFI ratio (lower).

The present invention provides a diagnostic method for diagnosing chronic inflammatory demyelinating polyneuropathy (CIDP). The CIDP which can be diagnosed by the present invention is a syndrome involving various pathological conditions as described above, and is roughly classified into typical CIDP and atypical CIDP. Typical CIDP represents a symmetric motor and sensory disorder that progresses for more than 2 months, in which proximal and distal muscles are simultaneously affected and tendon reflexes are reduced/disappear in the extremities. Cranial nerves may be impaired. Examples of atypical CIDP include DADS, MADSAM, a focal type, a pure sensory type, and a pure motor type.

According to the diagnostic method of the present invention, it is possible to extract a disease having homogeneous or relevant pathophysiologies from CIDP cases in which such numerous heterogeneous diseases coexist. This makes it possible to provide a more appropriate therapeutic regimen.

[Diagnostic Subject]

In the diagnostic method of the present invention, the diagnostic subject is any animal capable of suffering from chronic inflammatory demyelinating polyneuropathy (CIDP), such as a human, a non-human primate, a dog, a cat, a rabbit, a rat, or a mouse. Hereinafter, it will be explained for a human, but the same applies to other animals.

In the following description, in the case of referring to neurofascin 155 (NF155) or neurofascin 186 (NF186), it means human NF155 or human NF186, and in the case of referring to an anti-NF155 antibody or an anti-NF186 antibody, it means an antibody that binds to human NF or human NF186.

[Neurofascin NF155 (NF155)]

Neurofascin NF155 (NF155) is a protein having a molecular weight of 155 kDa and localized in the myelin side of the paranode. Cell membrane protrusions of Schwann cells in the peripheral nervous system or of oligodendrocytes in the central nervous system surround the axon as many times like a loop, so that the myelin sheath is formed and this portion takes a structure of the insulator, which in turn contributes to saltatory conduction of electrical signals in nerve axons. The adhesion part between the axon and the myelin sheath is divided into a paranode, a juxtaparanode, and an internode.

[Neurofascin NF186 (NF186)]

Neurofascin NF186 (NF186) is a protein with a molecular weight of 186 kDa that is accumulated in a node. Between the adjacent myelin sheaths is called a node.

The respective amino acid sequences are set forth in SEQ ID NO: 1 (NF155) and SEQ ID NO: 2 (NF186).

[Sample]

The sample to be diagnosed in the present invention may be any of blood (whole blood, serum, or plasma), saliva, cerebrospinal fluid, other body fluids, various tissues, and the like of a subject to be diagnosed. The sample is preferably a serum or a cerebrospinal fluid.

[Measuring Method]

The method of measuring each antibody in a sample is not particularly limited as long as it is a method used for detecting and measuring an antibody as an immunoassay. For example, any conventional measuring method using an enzyme, a fluorescent substance, a radioactive substance, a coloring substance or the like as a labeling substance may be used, and a flow cytometry technique may be preferably used.

[Diagnostic Method]

The diagnostic method for diagnosing chronic inflammatory demyelinating polyneuropathy (CIDP) of the present invention includes a step of measuring an anti-NF155 antibody contained in a sample. In addition, the diagnostic method for diagnosing chronic inflammatory demyelinating polyneuropathy of the present invention preferably further includes a step of measuring an anti-NF186 antibody contained in the sample. This is because in the case where the anti-NF155 antibody is positive, the anti-NF186 antibody contained in the sample is measured, and if the anti-NF186 antibody is negative, it is found that the anti-NF155 antibody binds to a specific epitope of NF155 not found in NF186, thus making it possible to more reliably diagnose chronic inflammatory demyelinating polyneuropathy (CIDP).

In order to measure an anti-NF155 antibody and an anti-NF186 antibody, an antibody assay is preferably carried out using the flow cytometry technique described above. In the case where the flow cytometry technique is used, the antibody assay can be made using cells with forced expression of NF155 and cells with forced expression of NF186 and a secondary antibody. The secondary antibody is not particularly limited, but it is preferably a fluorescently labeled antibody as described in the Examples and more preferably a fluorescently labeled anti-human IgG antibody.

The flow cytometry technique can be easily carried out by a well-known method.

In the flow cytometry technique used in the present invention, for example, a fluorescently labeled anti-human IgG antibody is used. In the case where an antibody is present in a sample after bringing the sample into contact with cells, it is possible to count the number of cells having a fluorescently labeled antibody bound to the cells via the antibody contained in the sample, by means of an antigen-antibody reaction. In this manner, it is possible to determine whether or not an antibody is present in the sample. Equipment of the flow cytometry technique and required reagents are commercially available and therefore the flow cytometry can be easily carried out by those skilled in the art.

That is, the sample is brought into contact with cells with forced expression of NF155 and cells with forced expression of NF186. In the present invention, as described in detail in the Examples, cells with forced expression of NF155 or NF186 can be constructed by introducing a vector into which cDNA of human NF155 or NF186 has been incorporated into cells suitable for expressing NF155 or NF186.

According to the present invention, a flow cytometry technique using each of cells with forced expression of NF155 and NF186 as an antigen is provided, and it is found that an antibody reacting with NF155 is highly likely to be CIDP positive.

Further, the present inventors have found that an anti-NF155 antibody-positive CIDP case is a juvenile-onset condition that exhibits characteristic features of marked demyelination (delay of nerve conduction) from distal portions and nerve roots of peripheral nerves, a high degree of hypertrophy of nerve roots on MRI, and highly increased cerebrospinal fluid protein levels. Since this type of CIDP exhibits irreversible significant nerve hypertrophy from the beginning of the onset, in the case where an anti-NF155 antibody is positive from when the first symptoms appear, immunotherapy will be aggressively applied.

With respect to anti-NF155 antibody-positive CIDP, IgG4 is predominant in a subclass of the anti-NF155 antibody. Accordingly, in the case where IgG4 is predominant as a result of measuring the IgG subclass of the anti-NF155 antibody, it is more likely to cause nerve hypertrophy, so it becomes possible to introduce an aggressive immunotherapy from the beginning of the clinical condition. As used herein, the phrase "IgG4 is predominant" is intended to mean that the MFI ratio and delta MFI of IgG4 are highest among IgG subclasses.

Further, according to the diagnostic method of the present invention, it is also possible to distinguish between CIDP and Guillain-Barré syndrome (GBS). Initial attack of CIDP is difficult to distinguish from Guillain-Barré syndrome (GBS) which takes a monophasic course. However, according to the present invention, if a sample is positive for an anti-NF155 antibody, it is found that there is a high possibility that the suspected clinical condition takes a recurrent and progressive course and then becomes CIDP rather than GBS. If it is found to be positive for an anti-NF155 antibody and therefore it is found that there is a high possibility that the suspected clinical condition is CIDP rather than GBS, a continuous treatment with intravenous immunoglobulin therapy (IVIg), simple plasma exchange (PE), corticosteroid drugs, and other immunosuppressive drugs becomes necessary.

In addition, some of anti-NF155 antibody-positive CIDPs are combined with central nervous lesions. Such a case is also included in the category of CCPD and is considered to constitute a series of spectra of anti-NF155 antibody-positive CIDP/CCPD. In the case where CCPD develops in central nervous lesions, it is difficult to distinguish CCPD from multiple sclerosis (MS) which is a demyelinating disease that affects only central nerves, and an interferon beta (IFNβ) preparation effective for MS is ineffective in CCPD and exacerbates the symptoms in about 30% of cases as well. However, according to the present invention, it has been found that there is a high possibility that the suspected clinical condition can be diagnosed as CIDP rather than MS if a sample is positive for an anti-NF155 antibody. Therefore, also in MS cases, it is meaningful to measure an anti-NF155 antibody, upon the introduction of a disease modifying drug including IFNβ. Measurement of an anti-NF155 antibody is also necessary for CCPD which affects both central and peripheral nerves.

The present invention further provides a method for measuring an anti-NF155 antibody and/or an anti-NF186 antibody in a sample, including bringing a sample into contact with cells with forced expression of NF155 and cells with forced expression of NF186, and measuring the presence of an anti-NF155 antibody and an anti-NF186 antibody using a fluorescently labeled anti-human IgG antibody.

Details of the sample, cells with forced expression of NF155, cells with forced expression of NF186, and the like were as described above. According to such a method, it is possible to measure whether or not NF155 and/or NF186 are present in a sample and it is useful for the diagnosis of chronic inflammatory demyelinating polyneuropathy. Also, according to such a method, it is possible to distinguish chronic inflammatory demyelinating polyneuropathy (CIDP) from Guillain-Barré syndrome (GBS) and multiple sclerosis (MS).

[Kit for Diagnosing CIDP]

Next, the kit of the present invention will be described.

The kit for diagnosing chronic inflammatory demyelinating polyneuropathy of the present invention includes a cell line with forced expression of NF155. The kit may further include a cell line with forced expression of NF186.

By using such a kit, it is possible to easily carry out the diagnostic method for diagnosing chronic inflammatory demyelinating polyneuropathy of the present invention, and the method for measuring the presence of an anti-NF155 antibody and an anti-NF186 antibody of the present invention, as described above.

The kit for diagnosing chronic inflammatory demyelinating polyneuropathy of the present invention may further include a fluorescently labeled anti-human IgG antibody. By including such a fluorescently labeled anti-human IgG antibody, it is possible to carry out the diagnostic method for diagnosing chronic inflammatory demyelinating polyneuropathy of the present invention, and the method for measuring the presence of an anti-NF155 antibody and an anti-NF186 antibody of the present invention, by means of a flow cytometry technique as described above.

As described above, in order to carry out the foregoing methods by means of flow cytometry, the kit for diagnosing chronic inflammatory demyelinating polyneuropathy of the present invention may include reagents necessary for carrying out a flow cytometry technique.

[Biomarker]

Next, the biomarker of the present invention will be described. The biomarker of the present invention consists of an anti-NF155 antibody and can be used for the diagnosis of CIDP. With respect to this anti-NF155 antibody, for example, the following application examples are conceivable.

The biomarker of the present invention can be used not only for the diagnosis of chronic inflammatory demyelinating polyneuropathy but also for screening a prophylactic or therapeutic agent for chronic inflammatory demyelinating polyneuropathy.

Also, for example, in the case of using a drug of chronic inflammatory demyelinating polyneuropathy in tailor-made medicine, whether or not the drug is effective for a specific patient can be easily determined by using a biomarker.

That is, the amounts of a biomarker in a patient sample are compared before and after administration of such a drug. In the case where the amount of the biomarker after administration falls below the amount of the biomarker before administration, it can be determined that the drug is effective for the patient. In the case where the amount of the biomarker is the same before and after administration or the amount of the biomarker after administration is higher than before administration, it can be determined that the drug is ineffective for the patient.

Further, the biomarker of the present invention can be used as an indicator of the presence or absence of or the degree of progression of chronic inflammatory demyelinating polyneuropathy.

EXAMPLES

The present invention will be described more specifically with reference to the following Examples, but the Examples are examples of the present invention and do not limit the scope of the present invention.

In the following Examples, as a subject to be used as a sample, 50 CIDP cases, which satisfied the EFNS/PNS definite electrophysiological diagnostic criteria for CIDP, were used, among the cases visited and hospitalized at the Kyushu University Hospital between 2004 and 2014. In addition, CCPD cases were treated as CIDP this time since all of such CCPD cases had demyelinating peripheral neuropathy and satisfied diagnostic criteria of CIDP. As controls, 32 cases with multiple sclerosis (MS), 40 cases with peripheral neuropathies other than CIDP including 26 cases with Guillain-Barré syndrome (GBS)/Fisher syndrome (FS), and 30 healthy subjects (HCs) were used.

Sera were collected from the above-mentioned cases and then used in the Examples. Of 50 subjects with CIDP, typical cases were 36 subjects, and atypical cases were 14 subjects consisting of 5 subjects with DADS, 4 subjects with multifocal acquired demyelinating sensory and motor neuropathy (MADSAM), 2 subjects with focal type, 1 subject with pure motor type, and 2 subjects with pure sensory type. Four patients with anti-NF155 antibodies referred from other clinics were then added and evaluated according to their clinical signs. The results are 37 subjects in typical cases and 17 subjects in atypical cases, of which 8 for DADS, 4 for MADSAM, 2 for focal type, 1 for pure motor type, and 2 for pure sensory type. Among a total of 54 subjects, CIDP patients not having an anti-NF155 antibody were 41 subjects and CIDP patients having an anti-NF155 antibody were 13 subjects.

Example 1

Construction of cell line with forced expression of human NF155 and cell line with forced expression of human NF186

A vector containing human NF155 cDNA and a vector containing human NF186 cDNA were respectively purchased from OriGene Technologies, Inc. In each vector, a sequence encoding Turbo-GFP is incorporated at the C-terminal of each protein.

Each of the vectors was then linearized using the restriction enzyme ScaI. Specifically, ScaI manufactured by Takara Bio Inc. was used as ScaI, and the reaction was carried out as described in the package insert of Takara Bio Inc. Specifically, 2 µL of ScaI, 4 µL of 10×H buffer, 1.5 µg of substrate DNA, and sterilized purified water were added to make a total of 40 µL of solution, and the reaction was carried out at 37° C.

Each of the linearized vectors as described above was transfected into HK293 cells by lipofection using FuGENE 6 (manufactured by Roche Applied Sciences) according to the package insert. Subsequently, 1 mg/ml of G418 (manufactured by Life Technologies, Inc.) was added and the cells were cultured in DMEM to select a G418-resistant strain. The proliferated colonies were isolated using a cloning cylinder to obtain a cell line with forced expression of human NF155 and a cell line with forced expression of human NF186 cells, respectively.

Example 2

Measurement of Anti-NF155 Antibody Using Flow Cytometry Technique

Using FACS buffer 1 (DMEM, 1 mM EDTA, 1% FBS), HEK293 cells and NF155-expressing cells were respectively mixed to a cell density of $1 \times 10^6$/ml. 47.5 µL/well of the cell solution was placed in a 96-well microtiter plate, and then 2.5 µL/well of the CIDP patient serum was added and mixed therewith (serum dilution ratio of 1:20). Subsequently, the microtiter plate was incubated at 4° C. for 60 minutes, washed twice with 200 µL of FACS buffer 1, and then subjected to an antigen-antibody reaction with a secondary antibody (Alexa 647-conjugated anti-human IgG antibody, manufactured by Life Technologies, Inc.) (dilution ratio of 1:500), followed by incubation at 4° C. for 60 minutes. Subsequently, the plate was washed twice with 200 µL of FACS buffer 2 (PBS, 5 mM EDTA), and the ratio or difference (delta) of the mean fluorescence intensity (MFI) of the fluorescent secondary antibodies (Alexa 647) in each cell group was evaluated.

In the same manner as above, in a portion of an anti-NF155 antibody-positive serum sample, the presence or absence of anti-NF186 antibody was evaluated by flow cytometry and immunostaining techniques using an NF186-expressing cell line.

The cutoff value was set to 10 and 100 for MFI ratio and delta MFI ratio, respectively.

[Results]

The results of anti-NF155 antibody measurement (Example 2) by a flow cytometry technique are shown in FIG. 1A. The vertical axis and the horizontal axis of the graph indicate fluorescence intensities of Alexa 647 and Turbo-GFP, respectively. The view on the left side of FIG. 1A shows the results in a serum-free system. As is clear from FIG. 1A, HEK293 cells expressing human NF155 and HEK293 cells not expressing human NF155 could be separated into two cell populations by the fluorescence intensity of Turbo-GFP. The view on the left side shows an example in which only a secondary antibody is added without administering a patient serum, indicating that the fluorescence intensity of Alexa 647 is low in any of cell populations.

The middle view of FIG. 1A is a negative example. Although administration of a serum leads to a non-specifically increased fluorescence intensity of Alexa 647 in any of cell populations, the values of MFI ratio and delta MFI were 1.37 and 1.88, respectively, which were low values.

The view on the right side of FIG. 1A shows a positive example. The MFI ratio and the delta MFI were 48 and 276, respectively, which were significantly increased as compared with the negative example shown in the middle view of FIG. 1A.

Measurements were also carried out using a serially diluted serum. The results are shown in FIG. 1B. As clearly shown in the figure, it was confirmed that the value continuously changed.

Figure 2:
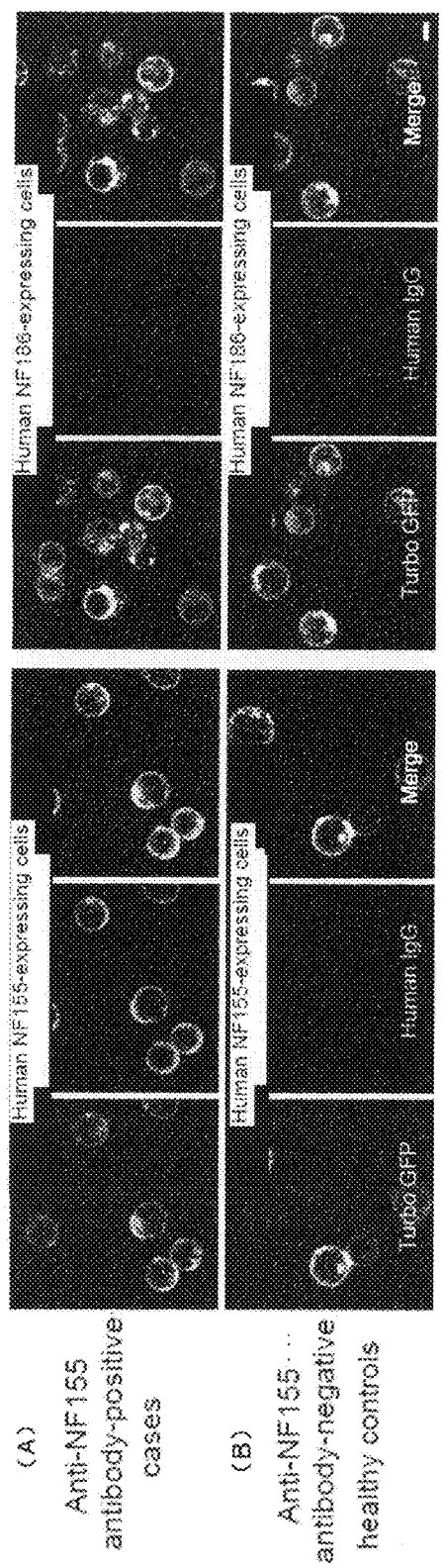
FIGS. 2A and 2B are the immunohistological results in the case where sera of anti-NF155 antibody-positive or negative CIDP patients were reacted with cells expressing human NF155 or human NF186. In each drawing, the left view shows a Turbo-GFP, the middle view shows a fluorescently labeled anti-human IgG antibody bound to IgG derived from a patient serum, and the right view shows the superimposition of both.

FIGS. 2A and 2B are the immunohistological results in the case where sera of anti-NF155 antibody-positive or negative CIDP patients were reacted with cells expressing human NF155 or human NF186, indicating that the serum of anti-NF155 antibody-positive CIDP patient reacted with the cells expressing human NF155 but not with the cells expressing human NF186.

Example 3

Detection of Anti-NF155 Antibody IgG Subclass

Using FACS buffer 1 (DMEM, 1 mM EDTA, 1% FBS), HEK293 cells and NF155-expressing cells were respectively mixed to a cell density of $1 \times 10^6$/ml. 47.5 µL/well of the cell solution was placed in a 96-well microtiter plate, and then 2.5 µL/well of patient serum was added and mixed therewith (serum dilution ratio of 1:20). Subsequently, the microtiter plate was incubated at 4° C. for 60 minutes, washed twice with 200 µL of FACS buffer 1, and then the following secondary antibodies were mixed with the cells at a dilution ratio of 1:500 to induce an antigen-antibody reaction.

The secondary antibodies used
PE-conjugated anti-IgG1 antibody (Cell Lab, 733179)
PE-conjugated anti-IgG2 antibody (Cell Lab, 736408)
PE-conjugated anti-IgG3 antibody (Cell Lab, 736487)
PE-conjugated anti-IgG4 antibody (Cell Lab, 733219)

After incubation at 4° C. for 60 minutes, the plate was washed twice with 200 µL of FACS buffer 2 (PBS, 5 mM EDTA), and the evaluation was made in terms of the ratio or difference (delta) of the mean fluorescence intensity (MFI) of the fluorescent secondary antibodies (PE) in each cell group.

[Results]

Figure 3:
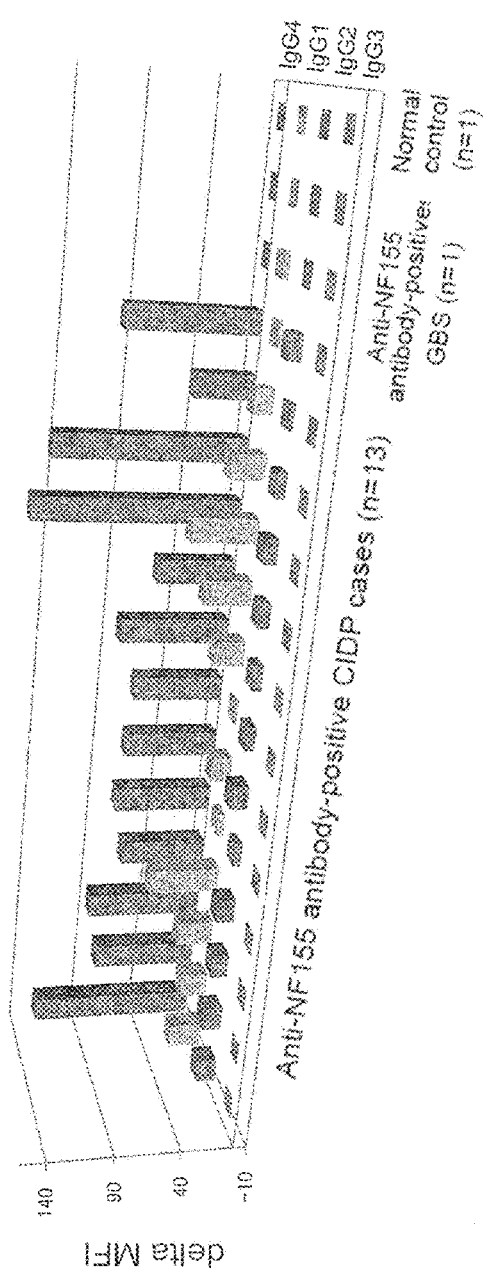
FIG. 3 is a view showing an IgG subclass of an anti-human NF155 antibody contained in a patient serum.

The results are shown in FIG. 3. As shown in FIG. 3, it was confirmed that IgG4 was predominant in all 13 cases subjected to experiments. On the other hand, IgG4 was not predominant in the anti-NF155 antibody-positive GBS case. From the above results, it was found that CIDP can be diagnosed with a higher probability by detecting the IgG subclass of anti-NF155 antibody.

Example 4

Figure 4:
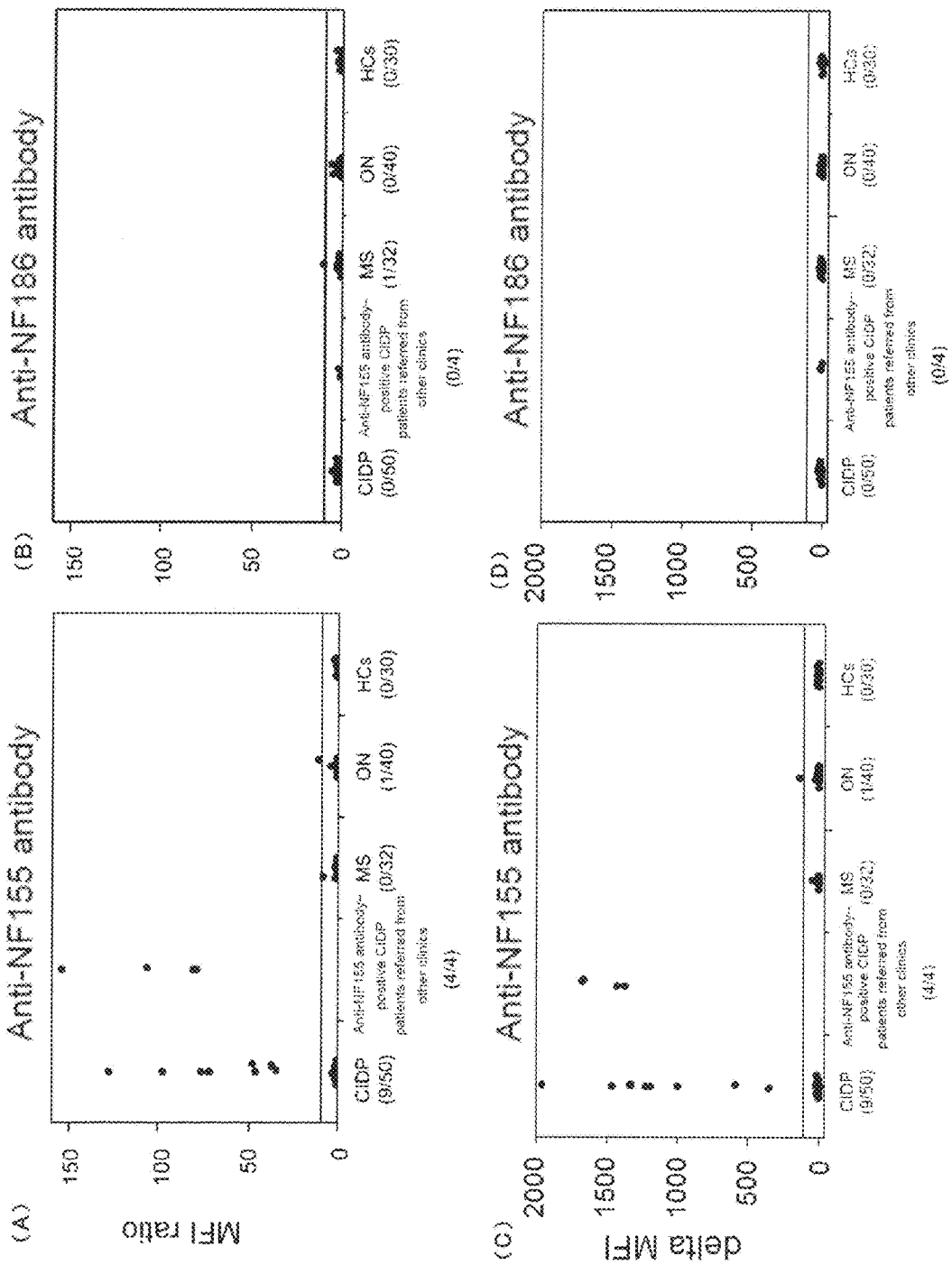
FIGS. 4A to 4D are views showing the results of detection of an anti-NF155 antibody and an anti-NF186 antibody for each case.

Using the same method as described in Example 2, anti-NF155 antibodies were measured in 50 patients diagnosed with CIDP by the definition according to electrophysiological criteria, and as control groups, in 4 anti-NF155 antibody-positive CIDP patients referred from other clinics, 32 patients with MS, 40 patients with ON (GBS/FS, vasculitic neuropathy, POEMS, HMSN, and anti-MAG antibody-positive neuropathy) and 30 HCs (healthy subjects). The results are shown in FIG. 4 and Table 1 below. The overall positivity rate was 18.0% (9/50). Among CIDPs, DADS type had a high positivity rate of 3/5 (60%), whereas there were no positive cases in nine other atypical CIDPs. In typical CIDP, the positivity rate was 16.7% (6/36). In the target group, the positivity rate was 0% (0/32) in multiple sclerosis (MS), 3.8% (1/26) in Guillain-Barré syndrome (GBS)/Fisher syndrome (FS), and 0% (0/30) in healthy subjects (HCs).

In addition, an anti-NF186 antibody was negative in any of cases.

TABLE 1

| Disease | n/N (%) |
|---|---|
| CIDP | 9/50 (18.0) |
| Typical CIDP | 6/36 (16.7) |
| Atypical CIDP | |
| DADS | 3/5 (60.0) |
| MADSAM | 0/4 (0.0) |
| Focal | 0/2 (0.0) |
| Pure motor | 0/1 (0.0) |
| Pure sensory | 0/2 (0.0) |
| MS | 0/32 (0.0) |
| GBS/FS | 1/26 (3.8) |
| Vasculitic neuropathy | 0/7 (0.0) |
| POEMS | 0/3 (0.0) |
| HMSN | 0/3 (0.0) |
| Anti-MAG antibody-positive neuropathy | 0/1 (0.0) |
| $HC_S$ | 0/30 (0.0) |

In the above Table 1,
CIDP = chronic inflammatory demyelinating polyneuropathy,
DADS = distal acquired demyelinating symmetric neuropathy,
FS = Fisher syndrome,
GBS = Guillain-Barré syndrome,
HCs = healthy controls,
HMSN = hereditary motor and sensory neuropathy,
MADSAM = multifocal acquired demyelinating sensory and motor neuropathy,
MAG = myelin-associated glycoprotein,
MS = multiple sclerosis,
n = number of positive cases,
N = number of cases collated, and
POEMS = polyneuropathy, organomegaly, endocrinopathy,
M protein, and skin changes (POEMS) syndrome.

Based on the fact that the anti-NF186 antibody was negative in any of anti-NF155 antibody-positive cases, it is assumed that the difference between NF155 and NF186 is generated by alternative splicing, so that the possible epitope is an amino acid sequence present in NF155 but not present in NF186.

Example 5

Clinical data were compared for anti-NF155-positive and negative CIDP cases. The results are shown in Table 2. In comparison with anti-NF155 antibody-negative CIDP (n=41), anti-NF155 antibody-positive CIDP (n=13) exhibited characteristic features of a younger onset age (25.2±10.7 versus 47.9±17.0, p<0.0001), a higher number of DADS types in which distal-dominant muscle weakness is conspicuous (46.2% versus 4.9%, p=0.0014), a higher ratio of drop foot (69.2% versus 31.7%, p=0.0242), a higher ratio of gait disturbance (100% versus 73.2%, p=0.0484), a higher ratio of tremor (53.8% versus 19.5%, p=0.0300), and a higher cerebrospinal fluid protein level (317.0±141.1 versus 103.8±75.8, p<0.0001).

Figure 5:
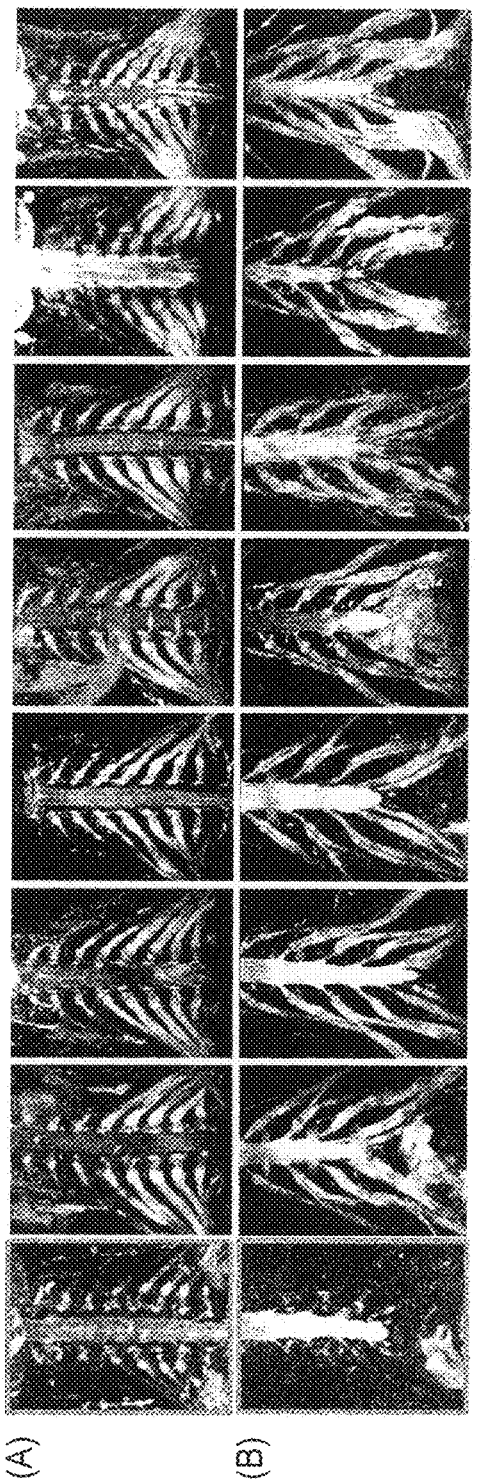
FIG. 5A is a view showing cervical MRI of seven anti-NF155 antibody-positive patients.
FIG. 5B is a view showing lumbar-sacral nerve root MRI of seven anti-NF155 antibody-positive patients.

The MRI results of the nerve root of the patients are shown in FIGS. 5A and 5B. As clearly shown in FIGS. 5A and 5B, marked hypertrophy of cervical and lumbar nerve roots, and proximal peripheral nerves was observed in all of 7 anti-NF155 antibody-positive CIDPs, thus demonstrating a characteristic clinical feature besides highly elevated protein levels in the cerebrospinal fluid.

Figure 6:
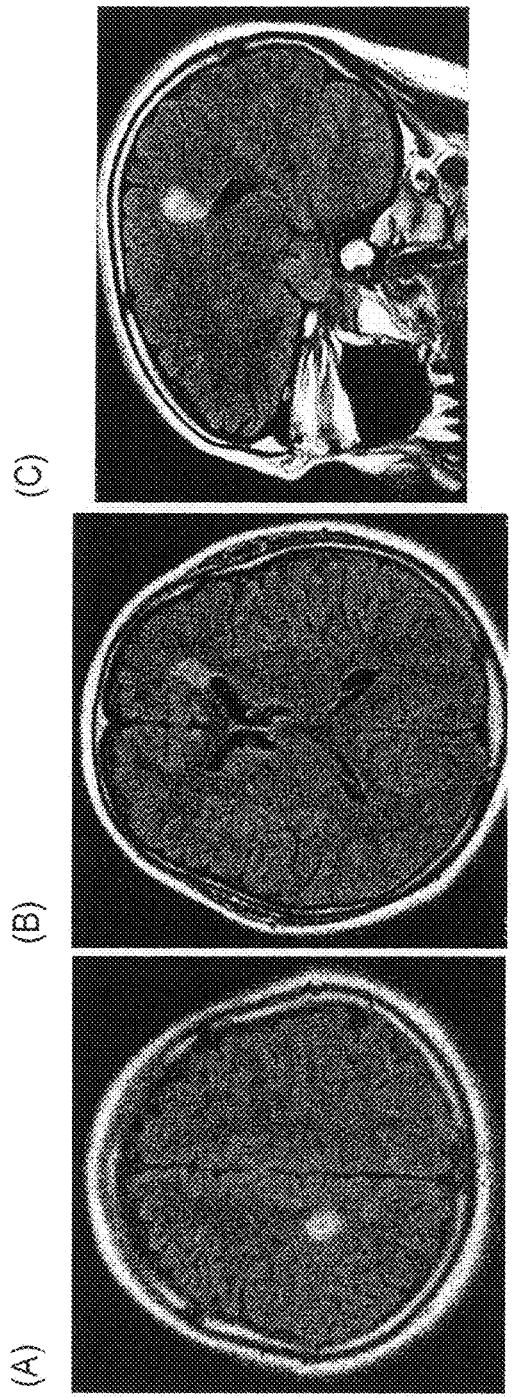
FIGS. 6A to 6C are views showing brain MRI of an anti-NF155 antibody-positive patient.
Figure 7:
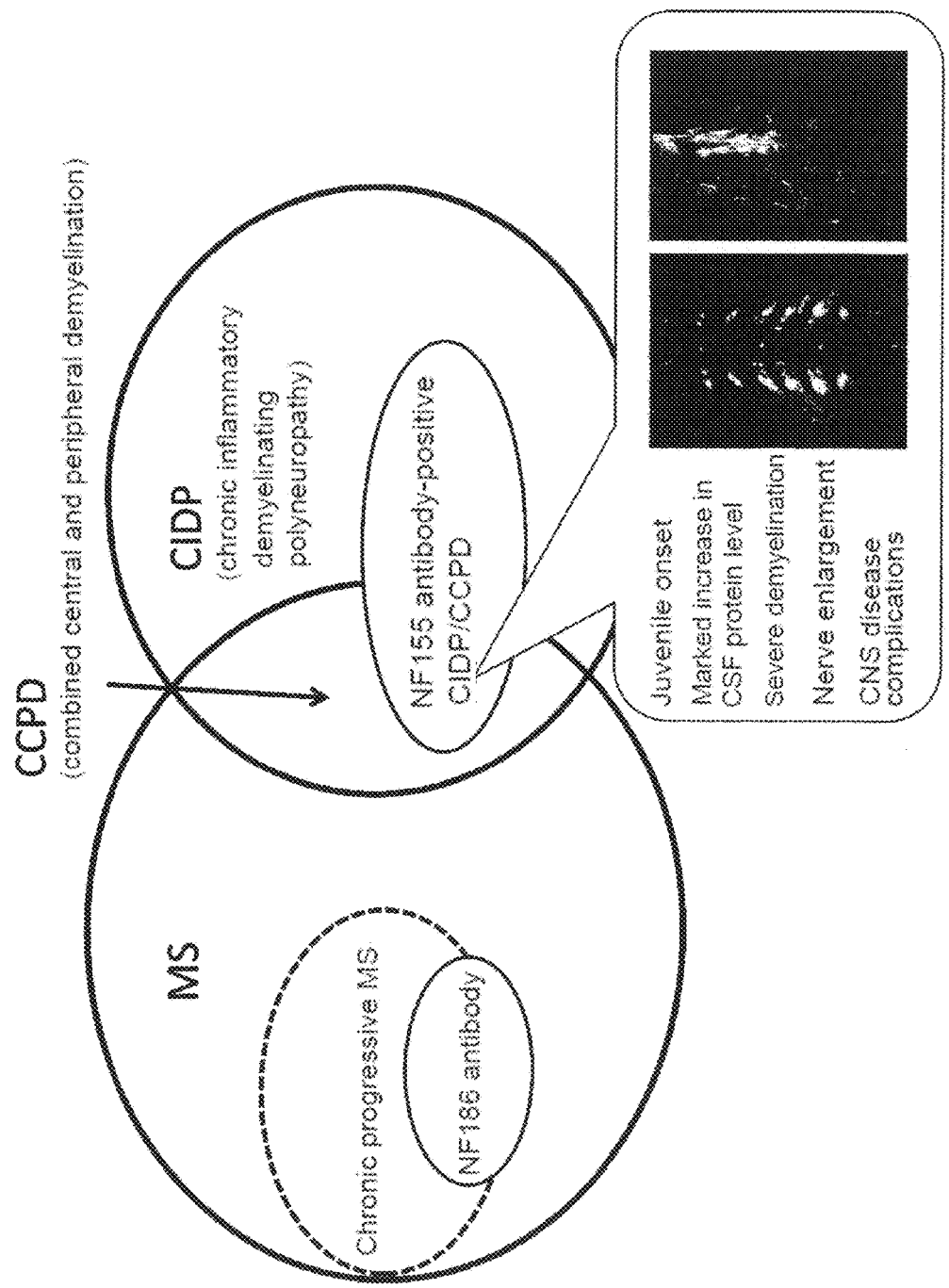
FIG. 7 is a view showing the positioning of an anti-human NF155-specific antibody in CIDP.

Further, brain MRI was carried out and the results are shown in FIGS. 6A to 6C. As shown in FIGS. 6A to 6C, there were cases in which demyelinating lesions were observed on brain MRI.

TABLE 2

|  | All patients | Anti-NF155 antibody-negative CIDPs | Anti-NF155 antibody-positive CIDPs | p-value |
|---|---|---|---|---|
| Demographics | N = 54 | N = 41 | N = 13 |  |
| Sex ratio (male:female) | 38:16 | 30:11 | 8:5 | NS |
| Age at onset (age range) (years) | 42.4 ± 18.4 (13-76) | 47.9 ± 17.0 (13-76) | 25.2 ± 10.7 (13-50) | <0.0001 |
| Age at examination (years) | 44.5 ± 19.3 | 50.3 ± 17.6 | 26.2 ± 11.9 | <0.0001 |
| Follow-up period (months) | 70.1 ± 94.2 | 70.5 ± 89.3 | 69.1 ± 112.2 | NS |
| Clinical phenotype | n/N (%) | n/N (%) | n/N (%) |  |
| Typical CIDP | 37/54 (68.5) | 30/41 (73.2) | 7/13 (53.8) | NS |
| DADS | 8/54 (14.8) | 2/41 (4.9) | 6/13 (46.2) | 0.0014 |
| MADSAM | 4/54 (7.4) | 4/41 (9.8) | 0/13 (0.0) | NS |
| Focal | 2/54 (3.7) | 2/41 (4.9) | 0/13 (0.0) | NS |
| Pure sensory | 2/54 (3.7) | 2/41 (4.9) | 0/13 (0.0) | NS |
| Pure motor | 1/54 (1.9) | 1/41 (2.4) | 0/13 (0.0) | NS |
| Hughes functional scale score | N = 54 | N = 41 | N = 13 |  |
| At the peak of illness | 2.31 ± 0.91 | 2.22 ± 0.88 | 2.62 ± 0.96 | NS |
| At the last visit | 1.63 ± 0.90 | 1.54 ± 0.90 | 1.92 ± 0.86 | NS |
| Mode of onset | n/N (%) | n/N (%) | n/N (%) |  |
| Acute | 0/54 (0.0) | 0/41 (0.0) | 0/13 (0.0) | NS |
| Subacute | 5/54 (9.3) | 4/41 (9.8) | 1/13 (7.7) | NS |
| Chronic | 49/54 (90.7) | 37/41 (90.2) | 12/13 (92.3) | NS |
| Clinical symptoms and signs | n/N (%) | n/N (%) | n/N (%) |  |
| Visual disturbance | 6/54 (11.1) | 3/41 (7.3) | 3/13 (23.1) | NS |
| Facial sensory disturbance | 10/54 (18.5) | 7/41 (17.1) | 3/13 (23.1) | NS |
| Facial palsy | 4/54 (7.4) | 2/41 (4.9) | 2/13 (15.4) | NS |
| Limb weakness | 52/54 (96.3) | 39/41 (95.1) | 13/13 (100) | NS |

TABLE 2-continued

|  | All patients | Anti-NF155 antibody-negative CIDPs | Anti-NF155 antibody-positive CIDPs | p-value |
|---|---|---|---|---|
| Upper-extremity muscle atrophy | 22/54 (40.7) | 19/41 (46.3) | 3/13 (23.1) | NS |
| Lower-extremity muscle atrophy | 24/54 (44.4) | 16/41 (39.0) | 8/13 (61.5) | NS |
| Drop foot | 22/54 (40.7) | 13/41 (31.7) | 9/13 (69.2) | 0.0242 |
| Gait disturbance | 43/54 (79.6) | 30/41 (73.2) | 13/13 (100) | 0.0484 |
| Cerebellar ataxia | 6/54 (11.1) | 4/41 (9.8) | 2/13 (15.4) | NS |
| Tremor | 15/54 (27.8) | 8/41 (19.5) | 7/13 (53.8) | 0.0300 |
| Disturbance of superficial sensation | 40/54 (74.1) | 32/41 (78.0) | 8/13 (61.5) | NS |
| Disturbance of deep sensation | 48/54 (88.9) | 35/41 (85.4) | 13/13 (100) | NS |
| Blood and cerebrospinal fluid tests | n/N (%) | n/N (%) | n/N (%) | |
| Monoclonal antibody | 3/49 (6.1) | 3/36 (8.3) | 0/13 (0.0) | NS |
| Antinuclear antibody ≥1:160 | 4/54 (7.4) | 2/41 (4.9) | 2/13 (15.4) | NS |
| Cerebrospinal fluid protein level (mg/dl) | 157.1 ± 132.9 | 103.8 ± 75.8 | 317.0 ± 141.1 | <0.0001 |
| Cerebrospinal fluid cell counts (/μl) | 3.2 ± 5.1 | 2.7 ± 5.5 | 4.9 ± 3.1 | NS |
| Cerebrospinal fluid albuminocytologic dissociation | 39/52 (75.0) | 32/39 (82.1) | 7/13 (53.8) | 0.0644 |
| Findings suggestive of inflammatory demyelination on MRI | n/N (%) | n/N (%) | n/N (%) | |
| Brain lesions | 6/40 (15.0) | 3/31 (9.7) | 3/9 (33.3) | NS |
| Spinal cord lesions | 3/31 (9.7) | 3/24 (12.5) | 0/7 (0.0) | NS |

All continuous variables are shown as mean ± SD.
In the above Table 2,
CIDP = chronic inflammatory demyelinating polyneuropathy,
DADS = distal acquired demyelinating symmetric neuropathy,
MADSAM = multifocal acquired demyelinating sensory and motor neuropathy,
n = number of cases involved,
N = number of cases collated,
NS = not significant, and
SD = standard deviation.

Example 6

A peripheral nerve conduction test was carried out in anti-NF155 antibody-positive and negative CIDP cases.

The comparison results of nerve conduction speed (NCS) findings of the anti-NF155 antibody-positive and negative CIDP cases are shown in Table 3.

TABLE 3

|  | All CIDPs | Anti-NF155 antibody-negative CIDPs | Anti-NF155 antibody-positive CIDPs | p-value |
|---|---|---|---|---|
| Median nerve | N = 92 | N = 71 | N = 21 | |
| Distal latency (ms) | 6.9 ± 3.0 (92/92) | 6.7 ± 3.3 (71/71) | 7.7 ± 1.4 (21/21) | NS |
| TLI | 0.36 ± 0.18 | 0.37 ± 0.19 | 0.32 ± 0.16 | NS |
| MCV (m/s) | 35.0 ± 12.2 | 35.7 ± 12.1 | 32.7 ± 12.4 | NS |
| CMAP amplitude (mV) | 4.7 ± 3.3 | 4.7 ± 3.7 | 4.7 ± 1.8 | NS |
| F-wave latency (ms) | 45.3 ± 13.6 (62/91) | 42.4 ± 11.4 (46/70) | 53.7 ± 16.3 (16/21) | 0.0033 |
| SCV (m/s) | 43.8 ± 9.7 (44/91) | 45.1 ± 8.8 (40/70) | 30.8 ± 10.1 (4/21) | 0.0038 |
| SNAP amplitude (μV) | 5.1 ± 3.7 | 5.3 ± 3.7 | 3.2 ± 2.9 | NS |

TABLE 3-continued

|  | All CIDPs | Anti-NF155 antibody-negative CIDPs | Anti-NF155 antibody-positive CIDPs | p-value |
|---|---|---|---|---|
| Ulnar nerve | N = 88 | N = 68 | N = 20 |  |
| Distal latency (ms) | 4.9 ± 1.8 (88/88) | 4.6 ± 1.8 (68/68) | 6.0 ± 1.1 (20/20) | 0.0009 |
| TLI | 0.46 ± 0.19 | 0.48 ± 0.19[c] | 0.42 ± 0.16 | NS |
| MCV (m/s) | 37.6 ± 13.5 | 39.0 ± 13.0 | 32.9 ± 14.3 | 0.0758 |
| CMAP amplitude (mV) | 4.2 ± 2.7 | 4.1 ± 2.9 | 4.3 ± 2.0 | NS |
| F-wave latency (ms) | 44.5 ± 17.0 (56/88) | 37.8 ± 8.4 (40/68) | 61.4 ± 21.2 (16/20) | <0.0001 |
| SCV (m/s) | 43.2 ± 9.0 (47/88) | 44.9 ± 7.5 (42/68) | 28.8 ± 7.6 (5/20) | <0.0001 |
| SNAP amplitude (µV) | 3.7 ± 3.0 | 4.0 ± 3.1 | 1.2 ± 0.97 | 0.0529 |
| Tibial nerve | N = 92 | N = 71 | N = 21 |  |
| Distal latency (ms) | 8.0 ± 4.2 (75/92) | 7.0 ± 3.7 (60/71) | 12.2 ± 3.8 (15/21) | 0.0001 |
| TLI | 0.49 ± 0.18 | 0.53 ± 0.17 | 0.31 ± 0.11 | <0.0001 |
| MCV (m/s) | 32.6 ± 9.8 | 33.7 ± 9.6 | 28.5 ± 9.4 | 0.0741 |
| CMAP amplitude (mV) | 4.0 ± 4.4 | 4.8 ± 4.5 | 0.78 ± 1.8 | 0.0011 |
| F-wave latency (ms) | 64.3 ± 14.6 (44/92) | 62.3 ± 14.1 (39/71) | 79.7 ± 9.5 (5/21) | 0.0109 |
| Sural nerve | N = 93 | N = 71 | N = 22 |  |
| SCV (m/s) | 44.5 ± 6.1 (52/93) | 45.2 ± 6.4 (41/71) | 41.9 ± 3.9 (11/22) | NS |
| SNAP amplitude (µV) | 7.0 ± 5.8 | 6.6 ± 5.8 | 8.4 ± 5.9 | NS |

In the above Table 3,
CIDP = chronic inflammatory demyelinating polyneuropathy,
CMAP = compound muscle action potential;
MCV = motor nerve conduction velocity;
N = number of examined nerves;
NF = neurofascin;
SCV = sensory nerve conduction velocity;
SNAP = sensory nerve action potential;
TLI = terminal latency index,
n = number of cases involved,
N = number of cases collated,
NS = not significant, and
SD = standard deviation.
All continuous variables are shown as mean ± SD, with number of evoked nerves/number of examined nerves in parentheses.

Reference values of distal latencies: median nerve, 3.49±0.34 ms; ulnar nerve, 2.59±0.39 ms; tibial nerve, 3.96±1.00 ms. Reference values of MCV: median nerve, 57.71±4.9 m/s; ulnar nerve, 58.7±5.1 m/s; tibial nerve, 48.5±3.6 m/s. Reference values of CMAP amplitudes: median nerve, 7.0±3.0 mV; ulnar nerve, 5.7±2.0 mV; tibial nerve, 5.8±1.9 mV. Reference values of F-wave latencies: median nerve, 26.2±2.2 ms; ulnar nerve, 27.6±2.2 ms; tibial nerve, 47.7±5.0 ms. Upper limit of normal of distal latencies: median nerve, 4.2 ms; ulnar nerve, 3.4 ms; tibial nerve 6.0 ms. Lower limit of normal of MCV: median nerve, 48 m/s; ulnar nerve, 49 m/s; tibial nerve, 41 m/s. Lower limit of normal of CMAP amplitudes: median nerve, 3.5 mV; ulnar nerve, 2.8 mV; tibial nerve, 2.9 mV. Upper limit of normal of F-wave latencies: median nerve, 31 ms; ulnar nerve, 32 ms; tibial nerve, 58 ms. Lower limit of normal of SCV: median nerve, 44 m/s; ulnar nerve, 44 m/s; sural nerve, 45 m/s.

As is apparent from Table 3, it was found that the distal latencies in the ulnar and the tibial nerves, and the F-wave latencies in the median, ulnar and tibial nerves are significantly prolonged in the anti-NF155-positive CIDP as compared to the anti-NF155-negative CIDP.

Further, it was found that although combined central and peripheral demyelination (CCPD) mainly includes chronic inflammatory demyelinating polyneuropathy (CIDP) and multiple sclerosis (MS), CIDP and MS can be distinguished from each other based on the presence or absence of an anti-NF155 antibody in a sample.

Even in CIDP and Guillain-Barré syndrome (GBS), it was also found that both can be distinguished from each other based on the presence or absence of an anti-NF155 antibody in a sample. That is, it has been conventionally difficult to distinguish Guillain-Barre syndrome, which is a demyelinating disease that acutely affects peripheral nerves, at the first episode, from CIDP. However, according to the above results, if the anti-NF155 antibody of the present invention is positive, it has been found that there is a high possibility that the suspected clinical condition would recur and become CIDP, and it has been found that measurement of an anti-NF155 antibody is useful in distinguishing GBS from recurring CIDP.

The present invention has been described in detail with reference to particular embodiments, but it is apparent to those skilled in the art that various changes and modifications are possible within the range not departing from the spirit and the scope of the present invention. The present application is based on U.S. Provisional Application (62/105,313) filed on Jan. 20, 2015, the entire contents of which are incorporated herein by reference.

The invention claimed is:

1. A method for diagnosing and treating chronic inflammatory demyelinating polyneuropathy in a subject, said method comprising:
   a. obtaining a sample from the subject,
   b. determining if the sample contains an anti-neurofascin 155 antibody that is predominantly IgG4,
   c. diagnosing the subject with delay of nerve conduction in distal portions and nerve roots of peripheral nerves, hypertrophy of proximal portions and nerve roots of peripheral nerves, and increased cerebrospinal fluid protein levels as compared to the case where the anti-neurofascin 155 antibody is negative if the anti-neurofascin 155 antibody is present in the sample, and
   d. administering an effective amount of a drug for treating chronic inflammatory demyelinating polyneuropathy to the diagnosed subject.

2. The diagnostic method according to claim 1, further comprising measuring an anti-neurofascin 186 antibody contained in the sample.

3. The diagnostic method according to claim 2, comprising detecting an antibody which reacts with neurofascin 155, but does not react with neurofascin 186.

4. The diagnostic method according to claim 1, comprising bringing the sample into contact with cells with forced expression of neurofascin 155 and cells with forced expression of neurofascin 186 and measuring the presence of the anti-neurofascin 155 antibody and/or the anti-neurofascin 186 antibody using a fluorescently labeled anti-human IgG antibody.

5. The diagnostic method according to claim 4, which is carried out by a flow cytometry technique.

6. The diagnostic method according to claim 1, comprising distinguishing chronic inflammatory demyelinating polyneuropathy from Guillain-Barre syndrome or multiple sclerosis.

7. The diagnostic method according to claim 1, wherein the sample is blood or cerebrospinal fluid.

8. A method for measuring an anti-neurofascin 155 antibody that is predominantly IgG4 and/or an anti-neurofascin 186 antibody that is predominantly IgG4 in a sample, comprising bringing a sample into contact with cells with forced expression of neurofascin 155 and cells with forced expression of neurofascin 186 and measuring the presence of the anti-neurofascin 155 antibody that is predominantly IgG4 and the anti-neurofascin 186 antibody that is predominantly IgG4 using a fluorescently labeled anti-human IgG antibody, wherein the method is carried out by a flow cytometry technique.

9. The method according to claim 8, comprising selecting a sample in which an anti-neurofascin 155 antibody is present but an anti-neurofascin 186 antibody is absent.

10. The method according to claim 8, wherein the sample is blood or cerebrospinal fluid.

11. The method according to claim 8, wherein the forced expression is forced expression associated with drug resistance.

* * * * *

SEQUENCE LISTING

<160> NUMBER OF SEQ ID NOS: 2

<210> SEQ ID NO 1
<211> LENGTH: 1189
<212> TYPE: PRT
<213> ORGANISM: Homo sapiens

<400> SEQUENCE: 1

```
Met Ala Arg Gln Pro Pro Pro Trp Val His Ala Ala Phe Leu Leu
1               5                   10                  15

Cys Leu Leu Ser Leu Gly Gly Ala Ile Glu Ile Pro Met Asp Leu Thr
                20                  25                  30

Gln Pro Pro Thr Ile Thr Lys Gln Ser Ala Lys Asp His Ile Val Asp
            35                  40                  45

Pro Arg Asp Asn Ile Leu Ile Glu Cys Glu Ala Lys Gly Asn Pro Ala
        50                  55                  60

Pro Ser Phe His Trp Thr Arg Asn Ser Arg Phe Phe Asn Ile Ala Lys
65                  70                  75                  80

Asp Pro Arg Val Ser Met Arg Arg Ser Gly Thr Leu Val Ile Asp
                85                  90                  95

Phe Arg Ser Gly Gly Arg Pro Glu Glu Tyr Glu Gly Glu Tyr Gln Cys
                100                 105                 110

Phe Ala Arg Asn Lys Phe Gly Thr Ala Leu Ser Asn Arg Ile Arg Leu
                115                 120                 125

Gln Val Ser Lys Ser Pro Leu Trp Pro Lys Glu Asn Leu Asp Pro Val
        130                 135                 140

Val Val Gln Glu Gly Ala Pro Leu Thr Leu Gln Cys Asn Pro Pro Pro
145                 150                 155                 160

Gly Leu Pro Ser Pro Val Ile Phe Trp Met Ser Ser Ser Met Glu Pro
                165                 170                 175

Ile Thr Gln Asp Lys Arg Val Ser Gln Gly His Asn Gly Asp Leu Tyr
                180                 185                 190

Phe Ser Asn Val Met Leu Gln Asp Met Gln Thr Asp Tyr Ser Cys Asn
                195                 200                 205

Ala Arg Phe His Phe Thr His Thr Ile Gln Gln Lys Asn Pro Phe Thr
        210                 215                 220

Leu Lys Val Leu Thr Asn His Pro Tyr Asn Asp Ser Ser Leu Arg Asn
225                 230                 235                 240

His Pro Asp Met Tyr Ser Ala Arg Gly Val Ala Glu Arg Thr Pro Ser
                245                 250                 255

Phe Met Tyr Pro Gln Gly Thr Ala Ser Ser Gln Met Val Leu Arg Gly
                260                 265                 270

Met Asp Leu Leu Leu Glu Cys Ile Ala Ser Gly Val Pro Thr Pro Asp
        275                 280                 285

Ile Ala Trp Tyr Lys Lys Gly Gly Asp Leu Pro Ser Asp Lys Ala Lys
        290                 295                 300

Phe Glu Asn Phe Asn Lys Ala Leu Arg Ile Thr Asn Val Ser Glu Glu
305                 310                 315                 320

Asp Ser Gly Glu Tyr Phe Cys Leu Ala Ser Asn Lys Met Gly Ser Ile
                325                 330                 335

Arg His Thr Ile Ser Val Arg Val Lys Ala Ala Pro Tyr Trp Leu Asp
                340                 345                 350

Glu Pro Lys Asn Leu Ile Leu Ala Pro Gly Glu Asp Gly Arg Leu Val
        355                 360                 365
```

-continued

```
Cys Arg Ala Asn Gly Asn Pro Lys Pro Thr Val Gln Trp Met Val Asn
    370                 375                 380

Gly Glu Pro Leu Gln Ser Ala Pro Pro Asn Pro Asn Arg Glu Val Ala
385                 390                 395                 400

Gly Asp Thr Ile Ile Phe Arg Asp Thr Gln Ile Ser Ser Arg Ala Val
                405                 410                 415

Tyr Gln Cys Asn Thr Ser Asn Glu His Gly Tyr Leu Leu Ala Asn Ala
            420                 425                 430

Phe Val Ser Val Leu Asp Val Pro Arg Met Leu Ser Pro Arg Asn
        435                 440                 445

Gln Leu Ile Arg Val Ile Leu Tyr Asn Arg Thr Arg Leu Asp Cys Pro
    450                 455                 460

Phe Phe Gly Ser Pro Ile Pro Thr Leu Arg Trp Phe Lys Asn Gly Gln
465                 470                 475                 480

Gly Ser Asn Leu Asp Gly Gly Asn Tyr His Val Tyr Glu Asn Gly Ser
                485                 490                 495

Leu Glu Ile Lys Met Ile Arg Lys Glu Asp Gln Gly Ile Tyr Thr Cys
            500                 505                 510

Val Ala Thr Asn Ile Leu Gly Lys Ala Glu Asn Gln Val Arg Leu Glu
            515                 520                 525

Val Lys Asp Pro Thr Arg Ile Tyr Arg Met Pro Glu Asp Gln Val Ala
    530                 535                 540

Arg Arg Gly Thr Thr Val Gln Leu Glu Cys Arg Val Lys His Asp Pro
545                 550                 555                 560

Ser Leu Lys Leu Thr Val Ser Trp Leu Lys Asp Asp Glu Pro Leu Tyr
                565                 570                 575

Ile Gly Asn Arg Met Lys Lys Glu Asp Asp Ser Leu Thr Ile Phe Gly
            580                 585                 590

Val Ala Glu Arg Asp Gln Gly Ser Tyr Thr Cys Val Ala Ser Thr Glu
        595                 600                 605

Leu Asp Gln Asp Leu Ala Lys Ala Tyr Leu Thr Val Leu Ala Asp Gln
    610                 615                 620

Ala Thr Pro Thr Asn Arg Leu Ala Ala Leu Pro Lys Gly Arg Pro Asp
625                 630                 635                 640

Arg Pro Arg Asp Leu Glu Leu Thr Asp Leu Ala Glu Arg Ser Val Arg
                645                 650                 655

Leu Thr Trp Ile Pro Gly Asp Ala Asn Asn Ser Pro Ile Thr Asp Tyr
            660                 665                 670

Val Val Gln Phe Glu Glu Asp Gln Phe Gln Pro Gly Val Trp His Asp
        675                 680                 685

His Ser Lys Tyr Pro Gly Ser Val Asn Ser Ala Val Leu Arg Leu Ser
    690                 695                 700

Pro Tyr Val Asn Tyr Gln Phe Arg Val Ile Ala Ile Asn Glu Val Gly
705                 710                 715                 720

Ser Ser His Pro Ser Leu Pro Ser Glu Arg Tyr Arg Thr Ser Gly Ala
                725                 730                 735

Pro Pro Glu Ser Asn Pro Gly Asp Val Lys Gly Glu Gly Thr Arg Lys
            740                 745                 750

Asn Asn Met Glu Ile Thr Trp Thr Pro Met Asn Ala Thr Ser Ala Phe
        755                 760                 765

Gly Pro Asn Leu Arg Tyr Ile Val Lys Trp Arg Arg Arg Glu Thr Arg
    770                 775                 780

Glu Ala Trp Asn Asn Val Thr Val Trp Gly Ser Arg Tyr Val Val Gly
```

-continued

```
            785                 790                 795                 800
        Gln Thr Pro Val Tyr Val Pro Tyr Glu Ile Arg Val Gln Ala Glu Asn
                        805                 810                 815
        Asp Phe Gly Lys Gly Pro Glu Pro Glu Ser Val Ile Gly Tyr Ser Gly
                        820                 825                 830
        Glu Asp Tyr Pro Arg Ala Ala Pro Thr Glu Val Lys Val Arg Val Met
                        835                 840                 845
        Asn Ser Thr Ala Ile Ser Leu Gln Trp Asn Arg Val Tyr Ser Asp Thr
                        850                 855                 860
        Val Gln Gly Gln Leu Arg Glu Tyr Arg Ala Tyr Tyr Trp Arg Glu Ser
            865                 870                 875                 880
        Ser Leu Leu Lys Asn Leu Trp Val Ser Gln Lys Arg Gln Gln Ala Ser
                        885                 890                 895
        Phe Pro Gly Asp Arg Leu Arg Gly Val Val Ser Arg Leu Phe Pro Tyr
                        900                 905                 910
        Ser Asn Tyr Lys Leu Glu Met Val Val Asn Gly Arg Gly Asp Gly
                        915                 920                 925
        Pro Arg Ser Glu Thr Lys Glu Phe Thr Thr Pro Glu Gly Val Pro Ser
            930                 935                 940
        Ala Pro Arg Arg Phe Arg Val Arg Gln Pro Asn Leu Glu Thr Ile Asn
        945                 950                 955                 960
        Leu Glu Trp Asp His Pro Glu His Pro Asn Gly Ile Met Ile Gly Tyr
                        965                 970                 975
        Thr Leu Lys Tyr Val Ala Phe Asn Gly Thr Lys Val Gly Lys Gln Ile
                        980                 985                 990
        Val Glu Asn Phe Ser Pro Asn Gln Thr Lys Phe Thr Val Gln Arg Thr
                        995                 1000                1005
        Asp Pro Val Ser Arg Tyr Arg Phe Thr Leu Ser Ala Arg Thr Gln
                        1010                1015                1020
        Val Gly Ser Gly Glu Ala Val Thr Glu Glu Ser Pro Ala Pro Pro
                        1025                1030                1035
        Asn Glu Ala Thr Pro Thr Ala Ala Tyr Thr Asn Asn Gln Ala Asp
                        1040                1045                1050
        Ile Ala Thr Gln Gly Trp Phe Ile Gly Leu Met Cys Ala Ile Ala
                        1055                1060                1065
        Leu Leu Val Leu Ile Leu Leu Ile Val Cys Phe Ile Lys Arg Ser
                        1070                1075                1080
        Arg Gly Gly Lys Tyr Pro Val Arg Glu Lys Lys Asp Val Pro Leu
                        1085                1090                1095
        Gly Pro Glu Asp Pro Lys Glu Glu Asp Gly Ser Phe Asp Tyr Ser
                        1100                1105                1110
        Asp Glu Asp Asn Lys Pro Leu Gln Gly Ser Gln Thr Ser Leu Asp
                        1115                1120                1125
        Gly Thr Ile Lys Gln Gln Glu Ser Asp Asp Ser Leu Val Asp Tyr
                        1130                1135                1140
        Gly Glu Gly Gly Glu Gly Gln Phe Asn Glu Asp Gly Ser Phe Ile
                        1145                1150                1155
        Gly Gln Tyr Thr Val Lys Lys Asp Lys Glu Glu Thr Glu Gly Asn
                        1160                1165                1170
        Glu Ser Ser Glu Ala Thr Ser Pro Val Asn Ala Ile Tyr Ser Leu
                        1175                1180                1185
        Ala
```

-continued

```
<210> SEQ ID NO 2
<211> LENGTH: 1239
<212> TYPE: PRT
<213> ORGANISM: Homo sapiens

<400> SEQUENCE: 2
```

Met Ala Arg Gln Pro Pro Pro Trp Val His Ala Ala Phe Leu Leu
1               5                   10                  15

Cys Leu Leu Ser Leu Gly Gly Ala Ile Glu Ile Pro Met Asp Pro Ser
                20                  25                  30

Ile Gln Asn Glu Leu Thr Gln Pro Pro Thr Ile Thr Lys Gln Ser Ala
            35                  40                  45

Lys Asp His Ile Val Asp Pro Arg Asp Asn Ile Leu Ile Glu Cys Glu
50                  55                  60

Ala Lys Gly Asn Pro Ala Pro Ser Phe His Trp Thr Arg Asn Ser Arg
65                  70                  75                  80

Phe Phe Asn Ile Ala Lys Asp Pro Arg Val Ser Met Arg Arg Arg Ser
                85                  90                  95

Gly Thr Leu Val Ile Asp Phe Arg Ser Gly Gly Arg Pro Glu Glu Tyr
            100                 105                 110

Glu Gly Glu Tyr Gln Cys Phe Ala Arg Asn Lys Phe Gly Thr Ala Leu
        115                 120                 125

Ser Asn Arg Ile Arg Leu Gln Val Ser Lys Ser Pro Leu Trp Pro Lys
130                 135                 140

Glu Asn Leu Asp Pro Val Val Gln Glu Gly Ala Pro Leu Thr Leu
145                 150                 155                 160

Gln Cys Asn Pro Pro Gly Leu Pro Ser Pro Val Ile Phe Trp Met
                165                 170                 175

Ser Ser Ser Met Glu Pro Ile Thr Gln Asp Lys Arg Val Ser Gln Gly
            180                 185                 190

His Asn Gly Asp Leu Tyr Phe Ser Asn Val Met Leu Gln Asp Met Gln
        195                 200                 205

Thr Asp Tyr Ser Cys Asn Ala Arg Phe His Phe Thr His Thr Ile Gln
210                 215                 220

Gln Lys Asn Pro Phe Thr Leu Lys Val Leu Thr Thr Arg Gly Val Ala
225                 230                 235                 240

Glu Arg Thr Pro Ser Phe Met Tyr Pro Gln Gly Thr Ala Ser Ser Gln
                245                 250                 255

Met Val Leu Arg Gly Met Asp Leu Leu Leu Glu Cys Ile Ala Ser Gly
            260                 265                 270

Val Pro Thr Pro Asp Ile Ala Trp Tyr Lys Lys Gly Gly Asp Leu Pro
        275                 280                 285

Ser Asp Lys Ala Lys Phe Glu Asn Phe Asn Lys Ala Leu Arg Ile Thr
290                 295                 300

Asn Val Ser Glu Glu Asp Ser Gly Glu Tyr Phe Cys Leu Ala Ser Asn
305                 310                 315                 320

Lys Met Gly Ser Ile Arg His Thr Ile Ser Val Arg Val Lys Ala Ala
                325                 330                 335

Pro Tyr Trp Leu Asp Glu Pro Lys Asn Leu Ile Leu Ala Pro Gly Glu
            340                 345                 350

Asp Gly Arg Leu Val Cys Arg Ala Asn Gly Asn Pro Lys Pro Thr Val
        355                 360                 365

Gln Trp Met Val Asn Gly Glu Pro Leu Gln Ser Ala Pro Pro Asn Pro
370                 375                 380

```
Asn Arg Glu Val Ala Gly Asp Thr Ile Ile Phe Arg Asp Thr Gln Ile
385                 390                 395                 400

Ser Ser Arg Ala Val Tyr Gln Cys Asn Thr Ser Asn Glu His Gly Tyr
            405                 410                 415

Leu Leu Ala Asn Ala Phe Val Ser Val Leu Asp Val Pro Pro Arg Met
        420                 425                 430

Leu Ser Pro Arg Asn Gln Leu Ile Arg Val Ile Leu Tyr Asn Arg Thr
    435                 440                 445

Arg Leu Asp Cys Pro Phe Phe Gly Ser Pro Ile Pro Thr Leu Arg Trp
450                 455                 460

Phe Lys Asn Gly Gln Gly Ser Asn Leu Asp Gly Gly Asn Tyr His Val
465                 470                 475                 480

Tyr Glu Asn Gly Ser Leu Glu Ile Lys Met Ile Arg Lys Glu Asp Gln
                485                 490                 495

Gly Ile Tyr Thr Cys Val Ala Thr Asn Ile Leu Gly Lys Ala Glu Asn
            500                 505                 510

Gln Val Arg Leu Glu Val Lys Asp Pro Thr Arg Ile Tyr Arg Met Pro
        515                 520                 525

Glu Asp Gln Val Ala Arg Arg Gly Thr Thr Val Gln Leu Glu Cys Arg
    530                 535                 540

Val Lys His Asp Pro Ser Leu Lys Leu Thr Val Ser Trp Leu Lys Asp
545                 550                 555                 560

Asp Glu Pro Leu Tyr Ile Gly Asn Arg Met Lys Lys Glu Asp Asp Ser
                565                 570                 575

Leu Thr Ile Phe Gly Val Ala Glu Arg Asp Gln Gly Ser Tyr Thr Cys
            580                 585                 590

Val Ala Ser Thr Glu Leu Asp Gln Asp Leu Ala Lys Ala Tyr Leu Thr
        595                 600                 605

Val Leu Ala Asp Gln Ala Thr Pro Thr Asn Arg Leu Ala Ala Leu Pro
    610                 615                 620

Lys Gly Arg Pro Asp Arg Pro Arg Asp Leu Glu Leu Thr Asp Leu Ala
625                 630                 635                 640

Glu Arg Ser Val Arg Leu Thr Trp Ile Pro Gly Asp Ala Asn Asn Ser
                645                 650                 655

Pro Ile Thr Asp Tyr Val Val Gln Phe Glu Glu Asp Gln Phe Gln Pro
            660                 665                 670

Gly Val Trp His Asp His Ser Lys Tyr Pro Gly Ser Val Asn Ser Ala
        675                 680                 685

Val Leu Arg Leu Ser Pro Tyr Val Asn Tyr Gln Phe Arg Val Ile Ala
    690                 695                 700

Ile Asn Glu Val Gly Ser Ser His Pro Ser Leu Pro Ser Glu Arg Tyr
705                 710                 715                 720

Arg Thr Ser Gly Ala Pro Pro Glu Ser Asn Pro Gly Asp Val Lys Gly
                725                 730                 735

Glu Gly Thr Arg Lys Asn Asn Met Glu Ile Thr Trp Thr Pro Met Asn
            740                 745                 750

Ala Thr Ser Ala Phe Gly Pro Asn Leu Arg Tyr Ile Val Lys Trp Arg
        755                 760                 765

Arg Arg Glu Thr Arg Glu Ala Trp Asn Asn Val Thr Val Trp Gly Ser
    770                 775                 780

Arg Tyr Val Val Gly Gln Thr Pro Val Tyr Val Pro Tyr Glu Ile Arg
785                 790                 795                 800
```

```
Val Gln Ala Glu Asn Asp Phe Gly Lys Gly Pro Glu Pro Glu Ser Val
            805                 810                 815

Ile Gly Tyr Ser Gly Glu Asp Leu Pro Ser Ala Pro Arg Arg Phe Arg
            820                 825                 830

Val Arg Gln Pro Asn Leu Glu Thr Ile Asn Leu Glu Trp Asp His Pro
            835                 840                 845

Glu His Pro Asn Gly Ile Met Ile Gly Tyr Thr Leu Lys Tyr Val Ala
850                 855                 860

Phe Asn Gly Thr Lys Val Gly Lys Gln Ile Val Glu Asn Phe Ser Pro
865                 870                 875                 880

Asn Gln Thr Lys Phe Thr Val Gln Arg Thr Asp Pro Val Ser Arg Tyr
            885                 890                 895

Arg Phe Thr Leu Ser Ala Arg Thr Gln Val Gly Ser Gly Glu Ala Val
            900                 905                 910

Thr Glu Glu Ser Pro Ala Pro Pro Asn Glu Ala Thr Pro Thr Ala Ala
            915                 920                 925

Pro Pro Thr Leu Pro Pro Thr Val Gly Ala Thr Gly Ala Val Ser
            930                 935                 940

Ser Thr Asp Ala Thr Ala Ile Ala Ala Thr Thr Glu Ala Thr Val
945                 950                 955                 960

Pro Ile Ile Pro Thr Val Ala Pro Thr Thr Ile Ala Thr Thr Thr
            965                 970                 975

Val Ala Thr Thr Thr Thr Thr Ala Ala Ala Thr Thr Thr Thr Glu
            980                 985                 990

Ser Pro Pro Thr Thr Thr Ser Gly Thr Lys Ile His Glu Ser Ala Pro
            995                 1000                1005

Asp Glu Gln Ser Ile Trp Asn Val Thr Val Leu Pro Asn Ser Lys
    1010                1015                1020

Trp Ala Asn Ile Thr Trp Lys His Asn Phe Gly Pro Gly Thr Asp
    1025                1030                1035

Phe Val Val Glu Tyr Ile Asp Ser Asn His Thr Lys Lys Thr Val
    1040                1045                1050

Pro Val Lys Ala Gln Ala Gln Pro Ile Gln Leu Thr Asp Leu Tyr
    1055                1060                1065

Pro Gly Met Thr Tyr Thr Leu Arg Val Tyr Ser Arg Asp Asn Glu
    1070                1075                1080

Gly Ile Ser Ser Thr Val Ile Thr Phe Met Thr Ser Thr Ala Tyr
    1085                1090                1095

Thr Asn Asn Gln Ala Asp Ile Ala Thr Gln Gly Trp Phe Ile Gly
    1100                1105                1110

Leu Met Cys Ala Ile Ala Leu Leu Val Leu Ile Leu Leu Ile Val
    1115                1120                1125

Cys Phe Ile Lys Arg Ser Arg Gly Gly Lys Tyr Pro Val Arg Glu
    1130                1135                1140

Lys Lys Asp Val Pro Leu Gly Pro Glu Asp Pro Lys Glu Glu Asp
    1145                1150                1155

Gly Ser Phe Asp Tyr Ser Asp Glu Asp Asn Lys Pro Leu Gln Gly
    1160                1165                1170

Ser Gln Thr Ser Leu Asp Gly Thr Ile Lys Gln Gln Glu Ser Asp
    1175                1180                1185

Asp Ser Val Asp Tyr Gly Glu Gly Gly Glu Gly Gln Phe Asn Glu
    1190                1195                1200

Asp Gly Ser Phe Ile Gly Gln Tyr Thr Val Lys Lys Asp Lys Glu
```

-continued

```
            1205                1210              1215
Glu Thr Glu Gly Asn Glu Ser  Ser Glu Ala Thr Ser  Pro Val Asn
        1220                1225              1230

Ala Ile Tyr Ser Leu Ala
    1235
```